(12) United States Patent
Gooberman

(10) Patent No.: US 6,203,813 B1
(45) Date of Patent: Mar. 20, 2001

(54) PHARMACEUTICAL DELIVERY DEVICE AND METHOD OF PREPARATION THEREFOR

(76) Inventor: Lance L. Gooberman, 35 Gill Rd., Haddonfield, NJ (US) 08033

( * ) Notice: Subject to any disclaimer, the term of this patent is extended or adjusted under 35 U.S.C. 154(b) by 0 days.

(21) Appl. No.: 09/169,042

(22) Filed: Oct. 9, 1998

Related U.S. Application Data

(63) Continuation-in-part of application No. 08/991,025, filed on Dec. 15, 1997, now abandoned, which is a continuation-in-part of application No. 08/829,003, filed on Mar. 31, 1997, now abandoned.

(60) Provisional application No. 60/028,605, filed on Jan. 13, 1997.

(51) Int. Cl.$^7$ .................................................. A61F 13/00
(52) U.S. Cl. ........................ 424/422; 424/423; 424/426; 514/255; 514/282; 514/812; 514/953; 514/965
(58) Field of Search ................................... 424/422, 423, 424/426; 514/255, 282, 812, 953, 965

(56) References Cited

U.S. PATENT DOCUMENTS

| | | | |
|---|---|---|---|
| 3,469,005 | 9/1969 | Weil et al. | 424/226 |
| 3,495,005 | 2/1970 | DeFelice et al. | 424/247 |
| 3,495,007 | 2/1970 | Thominet et al. | 424/282 |
| 3,625,214 | 12/1971 | Higuchi | 128/260 |
| 3,879,555 | 4/1975 | Pachter et al. | 424/260 |
| 3,887,699 * | 6/1975 | Yolles | 424/19 |
| 4,176,186 | 11/1979 | Goldberg et al. | 424/260 |
| 4,748,024 | 5/1988 | Leonard | 424/489 |
| 4,829,070 | 5/1989 | Bodor | 514/307 |
| 4,857,533 | 8/1989 | Sherman et al. | 514/282 |
| 4,863,928 | 9/1989 | Atkinson et al. | 514/282 |
| 4,877,791 | 10/1989 | Sherman | 514/282 |
| 4,880,921 | 11/1989 | Bodor | 540/110 |
| 4,882,335 | 11/1989 | Sinclair | 514/282 |
| 4,888,346 | 12/1989 | Bihari et al. | 514/282 |
| 4,889,860 | 12/1989 | Rzeszotarski et al. | 514/282 |
| 4,892,778 | 1/1990 | Theeuwes et al. | 428/218 |
| 4,897,268 | 1/1990 | Tice et al. | 424/422 |
| 4,900,555 | 2/1990 | Cheng et al. | 424/449 |
| 4,957,119 | 9/1990 | de Nijs | 128/832 |
| 5,021,241 | 6/1991 | Yamahira et al. | 424/426 |
| 5,088,505 | 2/1992 | de Nijs | 128/830 |
| 5,141,748 | 8/1992 | Rizzo | 424/425 |
| 5,176,907 * | 1/1993 | Leong | 424/78.08 |
| 5,326,568 | 7/1994 | Giampapa | 424/426 |
| 5,486,362 | 1/1996 | Kitchell et al. | 424/426 |
| 5,494,677 | 2/1996 | Giampapa | 424/426 |
| 5,629,009 | 5/1997 | Laurencin et al. | 424/426 |
| 5,789,411 | 8/1998 | Gooberman et al. | 514/255 |

OTHER PUBLICATIONS

Atkins, et al., Proc. Intern Symp. Control Rel. Bioact. Mater, 19:54 (1992).
Bardo, et al., Pharmacology, Biochemistry & Behavior, 28:267–273 (1987).
Bardo, et al., Neuropharmacology, 27(11):1103–1109 (1988).
Leafe, et al., Advances in Biochemical Psychopharmacology, 8(74):569–575 (1973).

(List continued on next page.)

*Primary Examiner*—Thurman K. Page
*Assistant Examiner*—Lakshmi Channavajjala
(74) *Attorney, Agent, or Firm*—Lerner, David, Littenberg, Krumholz & Mentlik, LLP

(57) ABSTRACT

The present invention provides an opiate antagonist implant which is an admixture of an opiate antagonist, in either acid or base form, and a pharmaceutically acceptable carrier. The admixture is uniformly compressed into a subcutaneously implantable pellet which is effective to release levels of the opiate antagonist over desired amounts of time when subcutaneously implanted in a patient to effectively inhibit the effects of a number of addictive drugs.

40 Claims, 1 Drawing Sheet

OTHER PUBLICATIONS

Maa, et al., J. Controlled Rel., 14:21–28 (1990).
Martin, Pharmacological Review, 19(4):463–521 (1967).
Pechnick, et al., Neuropharmacology, 26(11):1589–1593 (1987).
Ballard, Remington's Pharmaceutical Sciences, 1954 et seq. (1980).
Reuning, et al., Journal of Pharmacokinetics and Biopharmaceutics, 1(4)1:369–387 (1983).
Ringler, Steroids, 7(4):341–349 (Apr. 1966).
Roskos, et al., Clin. Mat., 13 (109–119) (1993).
Woodland, et al., Journal of Medicinal Chemistry, 16(8):897–901 (1973).
Yamaguchi, et al., Journal of Controlled Release, 19:299–314 (1992).
Yolles, et al. Industrial Medicine, 41(10):29–35 (Oct. 1972).
Yolles, Polymer Science and Technology, 8:245–261 (1975).
Yolles, et al., General Pharmaceutical Sciences, 64(1):115–116 (Jan. 1975).
Yolles, et al., Journal of Pharmaceutical Sciences, 64(2):348–349 (Feb. 1975).
Yolles, et al, Bulletin of the Parenteral Drug Association, 30(6):306–312 (Nov.–Dec. 1976).
Yolles, et al., Acta Pharm. Swec., 15:382–388 (1978).
Yolles, et al., Journal of a Parenteral Drug Association, 32(4) (Jul.–Aug. 1978).
Yoburn, et al., J. Pharmacol. Exp. Ther. 237(1):126–130 (1986).
Chiang, et al., Clin. Pharmacol. Ther., 36(5):704–708 (1984).
Sharon, et al., Naltrexone: Research Monograph 28, National Institute on Drug Abuse, R.E. Willette and G. Barnett, eds., 194–213(1980).
Misra, Naltrexone: Research Monograph 28, National Institute on Drug Abuse, R.E. Willette and G. Barnett, eds., 132–146 (1980).
Renault, Naltrexone: Research Monograph 28, National Institue on Drug Abuse, R.E. Willette and G. Barnett, eds., 11–22 (1980).
Wall, Chemistry and Life Sciences 12(6):677–682 (1984).
Wall, et al., Chemistry and Life Sciences Group, 9(4): 369–375 (1981).
Harrigan, et al., Naltrexone: Research Monograph 28, National Institute on Drug Abuse, R.E. Willette and G. Barnett, eds., 77–92 (1980).
Martin, William R., et al., Arch Gen Psychiatry, 28:784–791 (1973).
Cochin, et al., "The Influence of the Mode of Morphine Administration on Tolerance and Dependence," in *Problems of Drug Dependence*, 1979 Proceedings of the 41st Annual Scientific Meeting, The Committee on Problems of Drug Dependence, Inc.
Harris (ed.), NIDA Research Monograph 28 (1979).
Bardo, et al., Pharmacol. Biochem. Behav. , 21:591–597 (1984).
Misra, et al., Communications, J. Pham. Pharmac., 30:325–326 (1978).
Alim, et al., NIDA Research Monograph, 153, p. 253 (1995).
Bartter, et al., Am. J. Drug Alc. Abuse, 22(4):489–495 (1996).
Brewer, et al, Rapid Opiate Detoxification and Naltrexone Induction Under General Anesthesia and Assisted Ventilation: Experience with 510 Patients in Four Countries, Presented: The Royal College of Psychiatrists London, England (Jul., 1996).
Simon, J. Add. Dis., 16(1): 103–122 (1997).
Bhargava, et al., Gen. Pharmac. 25(1):149–155 (1994).
Brewer, Addiction Biology, 2:291–303 (1997).
Chiang, et al., Drug and Alcohol Dependence, 16:1–8 (1985).
Chiang, et al, Psychopharmacology Bulletin, 21(3):672–675 (1985).
Chiang, et al., NIDA Research Monograph, 149:196–197 (1995).
Freedman, The Journal of the American Medical Association, 202(3):191–194 (Oct. 16, 1967).
Greeley, et al., Psychopharmacology, 96:36–39 (1988).
Heller, et al., J. Controlled Release, 16:3–14 (1991).
Hollister, et al., Drug and Alcohol Dependence, 8:37–41 (1981).
Freedman, "Cyclazocine and Methadone in Narcotic Addiction," *The Journal of the American Mecial Association*, vol. 202, No. 3, pp. 191–194 (Oct. 16, 1967).
Greeley, et al., "Paradoxical analgesia induced by naloxane and naltrexone," *Psychopharmacology*, vol. 96, pp. 36–39 (1988).
Heller, et al., "Recent developments in the synthesis and utilization of poly (ortho esters)," *J. Controlled Release* vol. 16, pp. 3–14 (1991).
Hollister, et al., "Adversive Effects of Naltrexone in Subjects not Dependent on Opiates,"0 *Drug and Alcohol Dependence*, vol. 8, pp. 37–41 (1981).
Leafe et al., "Injection Method for Delivery of Long–Acting Narcotic Antogonist," *Advances in Biochemical Psychopharmacology*, vol. 8, No. 74, pp. 569–575.
Maa, et al., "Controlled Release of Naltrexone Pamoate from Linear Poly (Ortho Esters)", *J. Controlled Rel.*, vol. 14, pp. 21–28 (1990).
Martin, "Opioid Antagonists," *Pharmacological Reviews*, vol. 19, No. 4, pp. 463–521 (1967).
Pechnick, et al., "The Role of Opiate Receptors in the Potentiation of Pentobarbital Sleeping Time by the Acute and Chronic Administration of Opiates," *Neuropharmacology*, vol. 26, No. 11, pp. 1589–1593 (1987).
Ballard, "Prolonged–Action Pharmaceuticals," *Remington's Pharmaceutical Sciences*, pp. 1594 et seq. (1980).
Reuning, et al., "Pharmacokinetic Quantitation of Naltrexone Controlled Release from a Copolymer Delivery System," *Journal of Pharmacokinetics and Biopharmaceutics*, vol. 11, No. 4, pp. 369–387 (1983).
Ringler, "Efficacy of Topically Applied Progestational Agents," *Steroids*, Vo. 7, No. 4, pp. 341–349 (Apr. 1966).
Roskos et al., "A Morphine–Triggered Delivery System in the Treatment of Heroin Addiction," *Clin. Mat.*, vol. 13, No. 109–119 (1993).
Woodland et al., "Long–Acting Delivery Systems for Narcotic Antagonist," *Journal of Medicinal Chemistry*, vol. 16, No. 8, pp. 897–901 (1973).
Yamaguchi, et al., "Biocompatibility studies of naltrexone sustained release formulations," *Journal of Controlled Release*, vol. 19, pp. 299–314 (1992).
Yolles, et al., "A Psychiatrist Looks at Drug Abuse," *Industrial Medicine*, vol. 41, No. 10, pp. 29–35 (Oct. 1972).

Yolles, "Controlled Release of Biologically Active Agnets," *Polymer Science and Technology*, vol. 8, pp. 245–261 (1975).

Yolles, et al., "Timed–Release Depot for Anti–Cancer Agents," *General Pharmaceutical Sciences*, vol. 64, No. 1, pp. 115–116 (Jan. 1975).

Yolles, et al., "Long Acting Delivery Systems for Narcotic Antogonists II: Release Rates of Naltrexone from Poly(lactic Acid) Composites," *Journal of Pharmaceutical Sciences*, vol. 64, No. 2, pp. 348–349 (Feb. 1975).

Yolles, et al., "Controlled Release of Biologically Active Drugs," *Bulletin of the Parenteral Drug Association*, vol. 30, No. 6, pp. 306–312 (Nov.–Dec. 1976).

Yolles et al., "Timed–released depo for anticancer agents. II.," *Acta Pharm. Swec.*, vol. 15, pp. 382–388 (1978).

Yolles et al., "Time–Release Depo for Anticancer Drugs: Release of Drug Covalently Bonded to Polymers," *Journal of a Parenteral Drug Association*, vol. 32, No. 4 (Jul.–Aug. 1978).

Atkins, et al., "An Injectable 30–Day Naltrexone Delivery System," *Proc. Intern Symp. Control Rel. Bioact. Mater*, 19:54 (1992).

Bardo, et al., "Chronic Naltrexone Supersensitize the Reinforcing and Locomotor–Activating Effects of Morphine," *Pharmacology, Biochemistry & Behavior*, vol. 28, pp. 267–273 (1987).

Bardo, et al., "Chronic Treatment with Naltrexone Enhances Morphine–Stimulated Dopamine Neurotransmission: Neurochemical and Behavioral Evidence," *Neuropharmacology*, vol. 27, No. 11, pp. 1103–1109 (1988).

Bhargava, et al., "Effects of Naltrexone Pellet Implantation on Morphine Tolerance and Physical Dependence in the Rat," *Gen. Pharmac.*, vol. 25, No. 1, pp. 149–155 (1994).

Brewer, "Ultra–rapid, antagonist–precipitated opiate detoxification under general anaesthesia or sedation," *Addiction Biology*, 2, 291–303 (1997).

Chiang, et al., "Clinical Evaluation of a Naltrexone Sustained–Release Preparation," *Drug and Alcohol Dependence*, vol. 16, pp. 1–8 (1985).

Chiang, et al., "Implantable Narcotic Antagonists: A Possible New Treatment for Narcotic Addiction," *Psychopharmacology Bulletin*, vol. 21, No. 3, pp. 672–675 (1985).

Chiang, et al., "Bioerodible Polymer Drug Delivery Systems," Medications Development for the Treatment of Pregnant Addicts and Their Infants, *NIDA Research Monograph*, 149, 196–197 (1995).

* cited by examiner

PHARMACEUTICAL DELIVERY DEVICE AND METHOD OF PREPARATION THEREFOR

This application is a continuation-in-part of U.S. application Ser. No. 08/991,025, filed on Dec. 15, 1997 now abandoned, which is a continuation-in-part of U.S. application Ser. No. 08/829,003, filed Mar. 31, 1997 now abandoned, which claims the benefit of U.S. Provisional Application No. 60/028,605, filed on Jan. 13, 1997.

FIELD OF THE INVENTION

The present invention relates to pharmaceutical delivery device in which the active ingredient is a pharmaceutically active substance and is effective as a self-sustaining delivery mechanism for its own dissolution and delivery for desired extended periods of time. More particularly, this invention relates to a subcutaneously implantable pellet produced in a novel compression method to form a concentrated implantable pharmaceutically active substance, and when subcutaneously inserted in a patient will deliver an effective and desired level of pharmaceutically active substance in the patient's bloodstream, preferably in excess of thirty days or more, and more preferably up to and exceeding ninety days.

The invention further relates to a pharmaceutical delivery device in the form of an opiate antagonist implant in which the active ingredient antagonist is effective as a self-sustaining delivery mechanism for its own dissolution and delivery for the desired extended periods of time. The invention also relates to such an implant in the form of a pellet produced by an inventive compression method to form an antagonist-containing subcutaneously implantable pellet which is capable of delivering an effective and desired level of antagonist in a patients bloodstream over desired extended period, preferably exceeding ninety days and longer.

BACKGROUND OF THE INVENTION

Heroin addiction is a growing health care problem in the United States. The United States Department of Health and Human Services' Substance Abuse Branch issued a report in December of 1994 stating that the number of emergency department visits directly related to heroin use rose from 48,000 in 1992 to 63,000 in 1993, a 31% increase. The rate of heroin-related episodes per 100,000 people rose 81%, from 15 to 28 per 100,000, between 1990 and 1993. Upon breaking down the heroin-using population into ethnic groups and age groups, it has been demonstrated that all subsets have increased rates of use for this time period.

Human opiate detoxification has been in use for some time. More than 31,000 individuals of the Empire Blue Cross and Blue Shield subscriber base in New York were hospitalized at least once for opiate dependency between 1982 and 1992. The majority of these individuals were working adults, and their principal reason for hospitalization was addiction treatment. Drug detoxification accounted for 96% of the admissions, and the length of stay ranged between five and ten days.

In cases where individuals have been recently "detoxed" there is a high incident of relapse and re-addiction. While these former addicts are often strongly motivated to seek treatment and relapses often produce quilt and depression, they are still unable to resist giving in to the intense craving for heroin or pressure from drug dealers.

In recognition of the foregoing, opiate antagonists have been administered to such detoxified addicts. Opiate antagonists are defined as chemical compounds which block the effects of opiate drugs by blocking the opiate receptors in a patient. By blocking the effects of agonist opiates, opiate antagonists also prevent the development of physical dependence and tolerance to opiate drugs, such as heroin.

It should be noted that while opiate antagonists do not produce symptoms when they are used in the treatment of heroin dependence, they will precipitate an abstinence syndrome in individuals who are physically dependent on an opiate drug. By virtue of their affinity for the opiate receptors, they will compete with and oftentimes displace opiate agonists from the receptor sites. Accordingly, a heroin addict must be detoxified before he can be treated with an opiate antagonist. Once completely free of opiate drugs, however, no symptoms will be produced by the administration of the opiate antagonist.

One preferred antagonist used in the treatment of former heroin addicts is naltrexone (N-cyclopropylmethylnoroxy morphone). Naltrexone, such as some opiate antagonists, provides no euphoric effects and there are no observable pharmacological consequences when a patient stops taking the drug. For naltrexone treatment to be effective, sufficient levels of the drug must be maintained in the patient for a substantial period of time. This typically requires the patient to self-administer dosages of the drug several times a week.

A major problem with the use of opiate antagonists, such as naltrexone, in the treatment of opiate addiction has been patient compliance. This is frequently due to the patient's strong desire to experience the euphoric feeling which would otherwise be prevented by the presence of the opiate antagonist in his or her bloodstream. Thus, it has been said that rehabilitation of the patient is the first target. (Brewer, *Addiction Biology:* 2, 291–303 (1997)).

One solution for improving patient compliance and concomitant rehabilitation is the time-lapsed release of an antagonist such as naltrexone over a desirably long period of time. Several methods for implantable antagonists in animals for purposes other than to successfully treat opiate-addicted humans have been reported. For example, in PECHNICK et al., *Neuropharmacology,* 26(11):1589–1593 (1987), male rats injected with pentobarbital showed sleeping time to be increasingly antagonized after naltrexone administration by injection, but not in subjects implanted with a pellet of naltrexone. This study concluded that potentiation of pentobarbital sleeping time produced by opiates is mediated by opiate receptors, but did not show any development of tolerance. No indication of how the naltrexone pellets are made or their composition is provided in this study, except that the naltrexone pellets were obtained from the National Institute on Drug Abuse. While no clinical treatment program for humans is suggested, the article concludes with suggestion that the use of barbiturates by individuals chronically using opiates may have profound adverse consequences.

In BARDO et al., *Pharmacology, Biochemistry & Behavior,* 28:267–273(1987), rats implanted with a naltrexone pellet were shown to be devoid of morphine-induced conditioned place preference (CPP). Pellets of naltrexone freebase used in this study were also obtained from the National Institute on Drug Abuse. Nothing is mentioned as to pellet composition or method of manufacture. It was concluded that chronic naltrexone exposure produces behavioral supersensitivity to morphine-induced reinforcement and hyperactivity, and that the reinforcing efficacy of heroin is potentiated following chronic naltrexone administration. It was also concluded that up-regulation of opiate receptors following chronic naltrexone enhances opiate reward and that chronic naltrexone also potentiated morphine-induced hyperactivity in rats.

BARDO et al., *Neuropharmacology* 27(11): 1103–1109 (1988) also discusses rats implanted with naltrexone pellets for short time intervals (from one to ten days in this study). As in other references pellets were obtained from the National Institute on Drug Abuse, but nothing is mentioned as to methods of pellet manufacture or pellet composition. As shown in this study, one-day after pellet removal naltrexone-treated animals displayed an enhanced response of the synthesis of dopamine (DA), and that naltrexone removal after ten days showed no effect on morphine-induced changes to DA synthesis and locomotor activity to indicate that supersensitivity to morphine is transient.

GREELY et al., *Psychopharmacology*, 96:36–39 (1988) also examined the effects of pellet implantation of opiate antagonists naloxone and naltrexone, and of chronic administration of naloxone by subcutaneous injections in rats. In this study, 50 mg pellets of naloxone and naltrexone were employed containing 10 mg naloxone or naltrexone as base (significantly low compared to human dosages of 1000 mg or more). Procedures for manufacturing these pellets or their exact composition were not revealed. The results of this study were said to show that repeated painful stimulation results in analgesia in rats treated with an opiate antagonist.

In YAMAGUCHI et al., *Journal of Controlled Release*, 19:299–314 (1992), a study was performed with subcutaneous implantation of naltrexone sustained release preparations such as naltrexone-containing beads and microspheres in rats and rabbits to evaluate tissue rejection. As in other references discussed herein, the beads and microspheres were obtained from the National Institute of Drug Abuse and are said to based on a matrix of poly-(L(+)-lactic-co-glycolic acid, a composition found unacceptable for use in humans by CHIANG, infra. This study concluded that all of the tested implantable materials caused inflammatory responses.

In another rat-based study, HEMENDRA et al., *Gen. Pharmac.*, 25(1):149–155 (1994), showed the effects of pellets containing 10 or 30 mg of naltrexone base implanted for up to seven days on the development of tolerance and physical dependence on morphine in rats. Again, naltrexone pellets used in this study were obtained from the National Institute on Drug Abuse, but the reference is silent as to method for pellet production and composition. As concluded in this study, when left intact, naltrexone pellet implantation prevents naltrexone-induced decrease in body temperature, and increase in fecal and urinary output and inhibits body weight loss during abrupt withdrawal. The results are said to show that a single pellet of 10 mg of naltrexone can effectively block morphine tolerance and physical dependence in rats, and that such a procedure may be useful in studying biochemical, endocrinological, and immunological mechanisms involved in opiate addiction processes.

Other animal-based studies are REUNING et al., *J. of Pharmakinetics and Biopharmaceutics*, 11(4):369–387 (1983) (naltrexone-containing lactic acid/glycolic acid copolymer beads subcutaneously implanted in monkeys); SHARON et al., Research Monograph 28, National Institute on Drug Abuse (1980)(polylactic-co-glycolic acid bead-containing naltrexone implanted in mice); and HARRIGAN et al., Naltrexone Research Monograph 28, National Institute on Drug Abuse (1980) (naltrexone 75/25 dipalmitin/tripalmitin matrix rods, naltrexone/disodium carbonate/chronomer rods, and naltrexone lactic acid glycolic acid and copolymer beads implanted in monkeys).

None of the aforementioned studies, however, provide any teaching or guidance for the expectation of successful treatment of opiate-addicted humans with a subcutaneously implantable antagonist-containing pellet.

Indeed, studies undertaken with subcutaneous administration of naltrexone-containing beads in opiate-addicted humans have been shown to be unacceptable for clinical treatment. In CHIANG et al., "Clinical Evaluation of a Naltrexone Sustained-Release Preparation", *Drug and Alcohol Dependence*, 16:1–8 (1985), beads composed of copolymers of lactic acid and glycolic acids containing 70% naltrexone were administered (30 or more at a time) for periods of from 2–4 weeks in male humans. To minimize tissue reactions, the beads were dispersed in a circle of 2 inches in diameter of the implantation site. As concluded in this study, the results were thought to indicate that a sustained-release dosage which is capable of maintaining a constant naltrexone plasma level for one month can be clinically useful if sufficient plasma levels of naltrexone are sustained. Unfortunately, however, it was also concluded that the use of the lactic acid-glycolic acid bead dosage form was precluded from clinical usefulness in humans due to the incidence of tissue irritations of the naltrexone-containing beads. As further projected, it was thought that the results of this study would be useful in the development of an as yet unidentified, improved delivery system which is biocompatible and suitable for clinical use for the treatment of narcotic addiction.

See also, for example, CHIANG et al., "Implantable Narcotic Antagonists: A Possible New Treatment for Narcotic Addiction", *Psychopharmacology Bulletin* 21(3):672–675 (1985), also reporting the results of implantable naltrexone-containing beads or spheres composed of copolymers of lactic acid and glycolic acid, and which also concludes that the incidence of tissue irritation excludes clinical use of this bead dosage form.

In a recent CHIANG et al. study, "Medications development for the treatment of pregnant addicts and their infants", NIDA Research Monograph 149 (1995), bioerodible polymer technology involving implantable/injectable matrices to administer drugs are discussed. Again, despite attempts by several earlier studies (see ATKINS et al., "An injectable 30-day naltrexone delivery system", *Proc. Intern Symp. Control Rel. Bioact. Mater* 19:54 (1992); CHIANG et al. (1985) supra; MAA et al., "Controlled release of naltrexone pamoate from linear poly(ortho)esters", *J. Controlled Rel.* 14:21–28 (1990); ROSKOS et al., "A Morphine-Triggered Delivery System in the Treatment of Heroin Addiction", *Clin. Mat.* 13:109–119 (1993); and HELLER et al., "Recent developments in the synthesis and utilization of poly(ortho) esters", *J. Control Release* 16:3–14 (1991)), and others currently working on 30-day naltrexone delivery systems, none are clinically useful, and more research is necessary before a bioerodible drug delivery system for drug addiction can be commercialized.

The disappointing results of the CHIANG et al. studies ending in non-clinically useful subcutaneous dosage forms are not surprising in that adverse reactions of naltrexone leading to limited acceptance of the drug as a treatment for opiate-dependent persons had been earlier predicted. See HOLLISTER et al., "Adverse effects of Naltrexone in Subjects Not Dependent on Opiates", *Drug and Alcohol Dependence*, 8:37–41 (1981).

The CHIANG et al. naltrexone bead implants are further undesirable in that their manufacture is relatively complex and excessively costly.

Recently, U.S. Pat. No. 5,486,362 has disclosed a subcutaneous implantable drug delivery system said to useful for treating nicotine-addicted individuals which consists of a physical constraint modulation system ("PCMS") containing a drug substitute such as lobeline, a substituted piperidine compound obtained from dried leaves of the Indian tobacco herb *Lobelia inflata*. Lobeline is said to produce physiological effects similar to nicotine and thus is an effective nicotine substitute which assists individuals in lessening addiction to nicotine, albeit with some undesirable side effects. Other drug substitutes said to be deliverable include the opiate antagonist naltrexone. The PCMS system which contains and delivers the drug substitute is a biodegradable polymer suitable for subcutaneous injections, preferably microparticles suspended in a pharmaceutically acceptable vehicle just prior to subcutaneous injection to avoid the undesirable release of significant amounts of the drug substitute into the vehicle. Examples of polymers said to be preferred for use in the delivery system include poly(lactic/glycolic) and copolymers, which as shown above, have been found to be unacceptable forms for clinical delivery of naltrexone in the CHIANG studies.

In view of the above, an important need therefore exists for a time-lapse release of an antagonist which can be subcutaneously implanted in humans to provide therapeutic levels of antagonist to patients over extended periods of time to successfully treat various addictions.

An equally important need exists for a viable time-lapse release pharmaceutical delivery system which can also be subcutaneously implanted in humans or animals to provide therapeutic levels of pharmaceuticals or biologically active substances to patients over extended periods of time to treat a wide array of maladies or to deliver vitamins and/or nutraceuticals or other nutriments as desired.

Several devices attempting to fill this need have been reported but have not proved to be desirable and/or commercially reasonable for one or more reasons. For example, in U.S. Pat. No. 5,629,009 there is described a composition and method for the controlled release of certain water-soluble proteins which comprises a surface-eroding polymer matrix and a water-soluble bioactive factor(s)for the controlled administration of a bioactive substance to a local cell population. The composition is said to comprise a bioerodible pharmasurface-eroding polymer having the bioactive substance interdispersed throughout a surface-eroding polymeric matrix, which erodes in the biological environment to release the bioactive substance to the selected area. The surface-eroding polymers is said to have hydrophobic backbones and hydrophillic hydrolytic linkages which bioerode from the surface at a constant rate in a biological environment, and can include polyanhydrides and polyorthoesters. Specific polyanhydrides can be poly-bis-p-carboxyphenoxypropane anhydride (PCPP) and poly-bis-p-carboxymethane anhydride (PCPM). Articles made according to this invention can include implants for dispensing a water-soluble bioactive factor to a local cell population.

In U.S. Pat. No. 5,021,241, there is described a solid sustained-release composition in the form of a needle-like, bar-like shape which is said to consist of an active ingredient in a pharmaceutically biodegradable carrier, such as proteins in the form of collagen, gelatin, and mixtures thereof. The compositions are said to be useful for injection or implanting in a body for release-sustaining of the active ingredient to maintain a desired level of the active ingredient in blood or in a lesional region for a long period of time. The pharmaceutically acceptable biodegradable carriers are limited to those which can be absorbed and are subject to enzymoloysis in the body. Active ingredients and may include medicaments which are effective in small amounts and wherein their activity is promoted by sustained release, and particularly those which are unstable to heat. Specific examples of the active ingredients are plasminogen activator, prostaglandin, prostacyclines, various by-hormones, interferons and interlukens, tissue necrosis factor and other cytokines.

These compositions are described as being prepared by mixing an aqueous solution of the active ingredient with a biodegradable carrier to incorporate the active ingredient in the carrier matrix, and then drying the mixture to a shaped product having enough strength for administering to a living body. Drying may be affected by, for example, allowing it to simply stand or by spray-drying. As further stated, by controlling the temperature of the solution at room temperature or lower, or by which the temperature of the active ingredient can be kept at room temperature or lower, the active ingredient is kept out of danger of being damaged by heat instability.

Next, in U.S. Pat. No. 4,897,268, there is described a method of delivering an active ingredient into an animal's system at a constant rate over a long period of time, such as one and one-half to six months or longer. The composition is stated as comprising a blend of free flowing spherical particles obtained by individually microencapsulating quantities of ingredient in different copolymer excipients which are biodegraded at varying rates. As also stated, an effective amount of a microencapsuled blend may be administered to the animal parenterally, e.g., intravenously, intramuscularly, subcutaneously, intranasally, intraperitoneally, or by inhalation. It is further stated that a quantity of the particles are of a particular co-polymer excipient in which the core active ingredient is released quickly after injection to deliver the ingredient after an initial period, and whereby a second quantity of the particles are of a type of excipient in which delivery of the encapsulated ingredient begins as the first quantity's delivery begins to decline with a third quantity of ingredient which is encapsulated with a still different excipient which results in delivery beginning as delivery of the second quantity begins to decline. Such is accomplished by varying a lactide/glycolide ratio in a poly(D,L-lactide-co-glycolide) encapsulation, or by utilizing a combination of various polymers with different lactide/glycolide ratios.

U.S. Pat. No. 3,887,699, there is described a drug dispensed in a biodegradable polymeric material that can be formed to a solid shape, which is said to exude the drug to the surface of a polymeric article, or otherwise the drug will migrate from the interior of the polymeric material to the surface until the surface is covered with a layer of the drug and an equilibrium is established between the surface layer and the drug at the interior of the polymeric material, whereby partially or totally removing the surface will disturb the equilibrium, and further amounts of drug will then permeate to the surface until the equilibrium is reestablished. This cycle is said to repeat itself until the supply of drug has been exhausted from the polymeric material.

Polymers useful in this device are said to be naturally occurring polymers such as sugar phosphates, which are known to be biodegradable, and synthetic polymers such as polylactides and polyglycolic acids, which are also biodegradable, i.e., that they are attacked and broken down into smaller chemical species by substances found in mammals, such as enzymes.

As further stated, lactic acid copolymers are said to offer a degree of flexibility in choosing the life of a polymer matrix, since such can be controlled through the amount and type of co-monomer used. Illustrated examples provided of suitable copolymers are glycolide, betapropiolactone, tetramethylglycolide, betabutyrolactone, tetramethylglycolide, b-butyrolactone, gammabutyrolactone, pivalolactone, intramolecular cyclic esters of alphahydroxybuteric acid, alphahydroxy, isovaleric acid, alphahydroxycaproic acid, alphahydroxy ethylbuteric acid, alphahydroxy isocaproic, alphahydroxy betamethyl valeric acid, alphahydroxy heptonic acid, alphahydroxy octanic acid, alphahydroxy deccanoic acid, alphahydroxy myristic acid, alphahydroxy stearic acid, alphahydroxy ligocenic acid, and betaphenol lactic acid. As also described, polyglycolic acids are said to provide excellent biodegradable properties. Drugs are incorporated in the biodegradable polymeric materials to form the drug delivery vehicle.

In U.S. Pat. No. 3,625,214 there is disclosed a drug-delivery device for the prolonged delivery of drugs for any predetermined time release mode, such as increased or decreased release, constant, pulsing, sinusoidal, etc. The device is said to be fabricated by applying a drug coating of a desired thickness to a drug-impermeable film which is soluble in body fluid to form a drug matrix coating. The coated film is then rolled to form a "jelly roll" configuration which upon administration to the body the outermost extremities of the film gradually erode in body fluids to expose drug coating, which is also soluble in body fluids, to release the drug to body tissues. Different designs of the "drug spiral" are said to account for variable release modes. Drugs useful in this device include proteins such as insulin, desensitizing agents such as ragweed pollen antigens, hay fever, pollen antigens, dust and milk antigens, various vaccines such as smallpox, yellow fever, cholera, and scarlet fever, various antibiotics such as penicillin, tetracycline, nystatin and streptomycin, and sedatives such as sodium pentobarbital phenobarbital, and other drugs having the same or different physiological activity as above-mentioned.

Film or carrier materials are said to be preferably polymeric in nature, inclusive of gelatins, collagen, polyvinyl alcohol, or polybasic, linear, dibasic acid anhydrides of this formula:

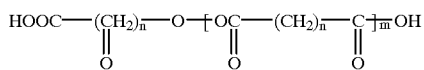

such as polyanhydride polymers of sebacic and azelaicacides, polyhydroxyacedic acids and poly sulfite polymers, or polymers that are cleaved by enzymes present in body fluids such as chitin which is enzymatically cleaved by lysozyme. The polyanhydride polymers are further described as being prepared by condensing respective dibasic acids in the presence of $SOCL_2$, benzene and ethyl acetate.

As also discussed these drug-delivery devices can be administered by implants, suppository, peroral pellets, oral bolus, vaginal pessary, buccal or sublingual lozenge, or ocular inserts.

Other prolonged-action pharmaceutical administration is discussed, for example, in *Remington's Pharmaceutical Sciences*, pp. 5094 et. seq. (1980). In this reference products are described as having properties of "sustained release", "prolonged action", and "repeat action". As discussed for example on page 1602, despite the fact that the taking of drugs by parenteral routes of administration is commonplace and many millions of dollars worth of parenteral products are sold annually for use in man there has been very little good research performed on the factors effecting absorption of drugs from parenteral sites of administration. This article also discusses the development and use of direct pellets in medical practice, and physical factors that have been suggested to effect implanted drug absorption rates including, inter alia, pellet density (hardness), crystal size used in making the pellet, and the influence of diluents. As further discussed, the densities of pellets made of pure drug depend upon factors such as the compression pressure used in making the pellets since absorption rates are directly proportional to the area of the pellet exposed to body fluids; other experiments are said to have shown that crystal size used in the manufacture of pure drugs have no effect in pellet absorption rates. As also stated, while pellet density and the size of the crystals used in pellet manufacture apparently have no effect on absorption rates the addition of a diluent to the formulation does have an effect. There are also many types of diluents and their modes of action are different in either enhancing or retarding drug absorption from implants. Unfortunately, as also mentioned, there are no general rules available for predicting absorption rates of a given drug diluent mixture, and thus there is no expectation of a successful implant over a given time period available, as such must be tested through trial and error.

In YOLLES et al., "Time-Release Depot for Anti-Cancer Patients", *General Pharmaceutical Sciences*, Vol. 64, Number 1, (January 1975) pp. 115 to 116, the controlled release of narcotic antagonist from composites made with poly (lactic acid) in film and in particle form is discussed. This paper undertakes an investigation to determine in vivo experiments of the amount of release of two particular anticancer agents from poly (lactic acid) composites. As shown hereinabove, however, in Chiang et al., implanted narcotic used in conjunction with beads and spheres composed of lactic acid co-polymers have been found unacceptable for use clinically.

Also, see for example, in YOLLES et al., "Long acting delivery systems for narcotic antagonists." *Journal of Pharmaceutical Sciences*, Vol. 64, No. 2, pp. 348–349 (February 1975), again discussing release rates of naltrexone from poly (lactic acid) composites.

Further, see WOODLAND et al., "Long-Acting Delivery Systems for Narcotic Antagonist", *Journal of Medicinal Chemistry*, Vol. 16, No. 8, pp. 897–901 (1973). This reference discusses composites of radioactive cyclazocine (2-cyclopropyl methyl-2 prime-hydroxide-5,9-dimethyl-6, 7-benzomorphan) with films of composite materials containing poly (lactic acid) of molecular weights ranging between 45,000 thousand and 70,000 thousand, to provide composites capable of releasing the drug cyclazocine for upwards of two months.

In YOLLES et al., "Controlled-Release of Biologically Active Drugs", *Bulletin of the Parenteral Drug Association*, Vol. 30, No.6, pp. 306 through 312, (November–December 1976) there is discussed a system of delivery of drugs at a controlled rate of a long period of time, perhaps months, which comprises the incorporation of a drug and a polyometric matrix and shaping the composite into a form such as a film, pellet or chip, and then implanting the structure into the body tissue of animals by surgery or hypodermic injection. The release rates, in vivo and in vitro, of progesterone, estradiol and three narcotic antagonist conclusive cyclazocine, naloxone, and naltrexone and two anticancer are studied. The polymer composites are again of non-desirable polylactic acid composition.

LEAFE et al., "Injection Method For Delivery of Long-Acting Narcotic Antagonist", *Advances in Biochemical*

Psychopharmacology, Vol. 8., No. 74, pp. 569–575 (Raven Press, New York, N.Y.) describes the hypodermic injection of a composite of cyclazocine-poly(lactic acid). In these tests the composite was hypodermically injected as a inspersion in carboxymethyl cellulose into the body tissue of rats.

In Yolles, "A Psychiatrist Looks at Drug Abuse" *Industrial Medicine,* Vol. 41, No. 10, pages 29–35 (October 1972), drug abuse and addiction in general are discussed. See further, YOLLES et al., "Time Released Depo for Anticancer Agents", *Acta Pharm. Swec.,* Vol. 15, pp. 382–388 (1978) discussing composites containing poly (lactic acid) and several anticancer agents; Yolles, "Time-Release Depo for Anticancer Drugs: Release of Drug Covalently Bonded to Polymers", *Journal of a Parenteral Drug Association,* Vol. 32, No. 4, (July–August 1978), discussing composites containing poly(lactic acid) and anticancer agents, namely cis dyeamine platinum (II), cyclophosphine, and dioxorubins; and Yolles, "Controlled Release of Biologically Active Agents", *Polymer Science and Technology,* Vol. 8, pages 245–261 (Plenum Press New York, N.Y. 1975) discussing the development of injectable systems for sustained delivery of drugs at controlled rates inclusive of release rates of naloxone and naltrexone, progesterone, and two anticancer drugs prepared by manufacturing composites of polymer (polyethylene or polylactic acid) and a plasticizer (tributal citrate), and melt pressing these composites into sheets containing a mixture of the drug and the polymer.

To date, none of the aforementioned drug delivery devices have been shown to be clinically useful and/or commercially viable.

SUMMARY OF THE INVENTION

To overcome the deficiencies of the above-described drug delivery devices, in one aspect, the present invention provides a subcutaneously implantable opiate antagonist and when implanted in a patient the antagonist is effective as a self-sustaining delivery mechanism for its own dissolution and for delivery over a desired extended period of time to effectively block the effects of heroin and/or other opiates, thus eliminating the craving response of addicts, and preventing re-addiction. The inventive implant is also useful in blocking the positive reinforcement from a number of other addictive substances including cocaine, alcohol, and nicotine. The opiate implant of the invention is effective to maintain sufficiently high levels of an opiate antagonist in a detoxified patient for an extended period of time, preferably at least about seventy-five days and longer in order to prevent a former addict from relapsing and to greatly aid in the rehabilitation of opiate-addicted patents.

The implant, which comprises an admixture of an opiate antagonist, an anti-inflammatory agent and a pharmaceutically acceptable carrier, is manufactured by compressing the admixture, preferably uniformly, into a subcutaneously implantable pellet containing antagonist in concentrated form, wherein such compressed admixture is effective to deliver therapeutically effective levels of an opiate antagonist when subcutaneously implanted over an extended period of time in a patient, for example, up to seventy-five days and longer.

In another aspect of this invention, there are provided subcutaneously implantable implants comprising any of a number of pharmaceutically and/or biologically active substances and drugs, including, but not limited to, protein drugs such as insulin, drugs used to treat rheumatoid arthritis and other forms of arthritis, antibiotics, and antiviral substances including anti HIV vaccines, deworming and distemper drugs such as those administered to pets and/or livestock, and drugs used for treating urinary tract infections, cancer-control/antineoplastic agents, vitamins and nutraceuticals, and any other pharmaceutical/ biologically active substances. In similar manner as their opiate antagonist-comprising counterparts, these inventive implants are effective to maintain the desired drug/substance levels for an extended period of time, up to and exceeding ninety days. These drug comprising implants are prepared from compressed admixtures comprising one or more drugs, an anti-inflammatory agent and a pharmaceutically acceptable carrier in the form of a subcutaneously implantable pellet.

This invention will be more fully described in the following detailed description of preferred embodiments, and accompanying examples.

DETAILED DESCRIPTION OF THE PREFERRED EMBODIMENTS

Figure 1:
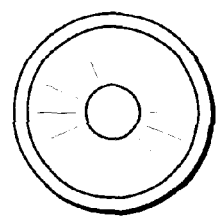
FIGS. 1–3 show a pellet press in cutaway perspective and cross-sectional views and its top portion comprising a die mold for forming pellets in accordance with this invention.
Figure 2:
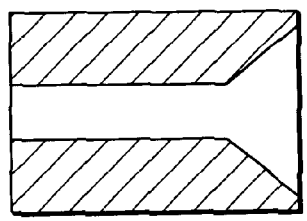
Figure 3:
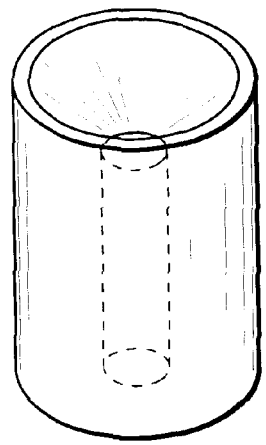

In its broadest sense, the present invention provides a novel delivery system comprising an admixture of a pharmaceutical/biologically active substance (active ingredient), an anti-inflammatory agent, and a pharmaceutically acceptable carrier compressed into a subcutaneously implantable pellet for implantation in a patient and effective for the delivery of therapeutically effective levels of the pharmaceutical/biologically active substance over extended periods of time, preferably in excess of ninety days.

By "pharmaceutical/biologically active substance" or otherwise "active ingredient" as used herein is meant any conventional, experimental, novel or as yet unknown pharmaceutical, drug or biologically active substance for use in animals or humans. Some examples include, without limitation: protein drugs such as insulin; desensitizing agents such as ragweed pollen antigens, hay fever pollen antigens, dust antigen and milk antigen; vaccines such as smallpox, yellow fever, distemper, hog cholera, fowl pox, antivenom, scarlet fever, diphtheria toxoid, tetanus toxoid, pigeon pox, whooping cough, influenza, rabies, mumps, measles, poliomyelitis, Newcastle disease, etc.; antiinfectives, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole; anti-virals including idoxuridine; and other antiinfectives including nitrofurazone and sodium propionate; antiallergenics such as antizoline, methapyrilene, chlorophenaramine, pyrilamine and prophenpyridamine; antiallergenics such as hydrocortisone, cortisone, hydrocortisone acetate, dexamethasone, dexamethasone 21-phosphate, fluocinolone, triamcinolone, medrisone, prednisolone, prednisolone 21-phosphate, and prednisolone acetate; decongestants such as phenylephrine, naphthazoline, and tetrahydrazoline; miotics and anticholinesterases such as pilocarpine, eserine salicylate, carbachol, diisopropyl fluorophosphate, phospholine iodide, and demecarium bromide; such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl)urea, carbromal; psychic energizers such as 3-(2 aminopropyl)indole acetate and 3-(2 amino butyl) indole acetate; Tranquilizers such as reserpine, chloropromaline, and thiopropazate; androgenic steroids such as methyltestosterone and fluorymesterone; estrogens such as estrone, 17 B-estradiol, ethenyl estradiol, and diethyl stilbesterol; progestational agents such as progesterone, megestrol, melengestrol, chlormadinone, ethisterone, norethynodrel, 19-nor-progesterone, norethindrone, medroxyprogesterone and 17 B-hydroxy-progesterone; Humoral agents such as the prostaglandins, for example $PGE_1$, $PGE_2$, and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine; antihistamines such as diphenhydramine, dimenhydrinate, tripelennamine, perphenazine, and chlorophenazine; cardioactive agents such as dibenzohydroflumethiazide, flumethiazide, chlorothiazide, and aminotrate; nutritional agents such as vitamins, essential amino acids and essential fats, and veterinary pharmaceuticals.

Other drugs having the same or different physiological activity as those recited above can be employed in drug-delivery devices within the scope of the present invention.

Drugs can be in various forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention an release characteristics but which are easily hydrolyzed by body pH, enzymes, etc., can be employed.

The amount of drug or bioactive substance incorporated in the drug-delivery device of the invention can vary widely depending on the particular drug, the desired therapeutic effect, and the time span for which it takes the subcutaneously implantable pellet to erode or dissolve. Since a variety of the inventive devices in a variety of sizes and shapes are intended to provide complete dosage regimes for therapy for a variety of maladies, there is no critical upper limit on the amount of drug incorporated in the device. The lower limit also will depend on the activity of the drug and the time span of its release from the device. Thus, it is not practical to define a range for the therapeutically effective amount of drug to be release by the device.

Other examples of active ingredients useful in the present inventive devices include medicaments which are effective in a very small amount and in which their activity is promoted by sustained release, and more particularly medicaments which are unstable to heat. Some examples of such active ingredients are tissue plasminogen activator, prostaglandins, prostacyclines, various bio-hormones, interferons, interleukins, tumor necrosis factor, and some other cytokines (e.g., macrophage activating factor, migration inhibitory factor and colony stimulating factor). The bio-hormones means substances which are produced within the living body and regulate the bio-functions, and include growth hormone (GH) such as human growth hormone (HGH), bovine growth hormone (bGH) including biosynthetic product (B-HGH, etc.); growth hormone releasing factors (GRF) which are known as peptides consisting of a number of amino acids of 44, 40, 37, or 29 (e.g., hGRF (1–44)$NH_2$, hGRF(1–29)$NH_2$); somatomedines (SM) such as SM-A, SM-B, SM-C, insulin-like growth factor (IGF)-I, IGF-II, and multiplication stimulating activity (MSA); and calcitonin (i.e. calcium regulating hormone secreted from the mammalian thyroid gland and in non-mammalian species from the ultimobranchial gland).

Interferon, interleukin, tumor necrosis factor, and some other cytokines are somewhat different each other, but are common in that they have very similar molecular weight and are glycoprotein or protein and have similar pharmacological and physicochemical properties.

The above active ingredients may be used alone or in combination of two or more thereof.

Additional examples of other active ingredients which can be incorporated to form an inventive device are further described below.

As is well known, people suffering from sugar diabetes are required to take daily doses of diabetes control agents. Insulin or the active ingredients in some of the commercially available control agents such as tolbutamide ("Orinase" by Upjohn), chloropropamine ("Diabinese" by Pfizer) and tolazamine ("Tolinase" by Upjohn) may be dispensed with an implantable device of this invention.

Many drugs are presently being used to treat rheumatoid arthritis and other forms of arthritis. These include, but are not limited to, narcotic pain relievers, gold salts, corticosteroids, adrenocorticotropic hormones, phenylbutazone and its derivatives, antimalarials, and indole derivatives. A comprehensive listing of specific drugs used to treat the various forms of arthritis is given in the Aug. 12, 1968 edition of *Chemical and Engineering News* at pp. 54 and 55, which listing is herein incorporated by reference. These drugs may be dispensed with the instant inventive implantable device.

Antibiotics are a further group of drugs which can be dispensed. Some examples of suitable antibiotics include the tetracylines, penicillin, streptomycin, and aureomycin.

Deworming and distemper drugs such as those given to household pets and/or cattle are another group of drugs capable of being dispensed by the device of this invention. An example of such a drug is phenothiazine.

Sulfur drugs such as sulfisoxazole diolamine ("Gantrisin" by Roche Laboratory), useful in treating urinary tract infections, could also be exuded from a crystalline polymeric article.

Another group of drugs suitable for use in the crystalline polymeric articles are cancer-control agents or otherwise known as antineoplastic compounds such as paclitaxel and Taxotere®. An example would be the drugs or combinations of drugs useful for treating leukemia such as the nitrogen mustard p-(di-2-chlorethyl) amino-phenylbutyric acid.

Two further groups of drugs which can be advantageously dispensed with the herein described device are alcoholaddition control agents and tobacco-smoking addiction control agents.

Closely related are the addictive drug antagonists. If an addictive drug such as heroin, morphine, codeine, neopine, etc. is taken while the blood still contains the antagonist, the addictive drug will pass through the body and be harmless to the taker in the sense that the taker will not experience "a high" and the drug will not be addictive. Such antagonists have offered a very successful method for treating drug addicts while the addicts are at clinics; however, it has been noted that once an addict returns to his original environment, and is out of control of the clinic, he is likely to stop taking the antagonist and resume taking one of the addictive drugs. For this reason, the implantable device of this invention offers unique advantages in treating drug addicts by this method, since the device containing an antagonist implanted within the addict's body provides him no control over the administering of the antagonist, thus extending the addict's period of cure beyond the time that he can actually be confined to a clinic. Some examples of specific drug antagonists suitable for incorporation into this inventive implant include N-allylnoroxymorphone ("naloxone") and 2-cyclopropylmethyl-2'hydroxy-5,9-dimethyl-6,7-benzomorphone ("cyclazocine" and "naltrexone"). Other drug control agents such as "methadone" can also be used.

Two further groups of closely related drugs are the thyroid gland regulating drugs and weight-control drugs. Here again, there is a particular advantage to the use of this inventive implant, since such a device can be implanted within the body of the patient and thereby supply the required amount of drug without the patient having any control over this. Also, it is known that these types of drugs are extremely dangerous when taken in large doses, and the use of this device would help assure that an overdose did not get into the patient's bloodstream.

Another group of drugs which could be dispensed are the analgesic drugs. These drugs have little or no therapeutic effect, but serve to lessen or eliminate the severe pain often encountered with many diseases or operations. For example, in the cases of chest cancer, morphine or codeine are often prescribed. Also, for patients suffering from cancer of the prostate glands, progesterone is often prescribed. One particularly advantageous use of the inventive implant is in serious surgical operations which result in severe pain to the patient after the operation is completed and the patient regains consciousness. In these cases, the body is going to be opened for the operation, and an implant device of this invention containing a pain killer can be inserted into the body during the operation to case the pain to the patient during the recovery period. Of course, there are many other types of analgesic drugs and any other examples of when such rugs could be used which will be apparent to those knowledgeable in the field of medicine.

Another group of drugs suitable for being dispensed from the inventive implant are the hormone-regulating drugs to aid fertilization or to act as contraceptives. One preferred embodiment using hormone-regulating drugs is formed using the active ingredients in oral contraceptives. The advantage is that a device containing the active ingredients of oral contraceptives could be designed to last over extended periods of time thereby relieving the taker from a daily routine of orally taking the contraceptives. Suitable examples of the active ingredients in oral contraceptives include a progestin or a combination of a progestin and an estrogen. For example, a homogeneous dispersion of the active ingredient in "Norethindrone" and "Mestranol" in a ration of 20:1 by weight could be prepared and incorporated into the solid polymeric material. Other examples of synthetic progesterones and estrogens suitable for use with this invention include: norethynodrel, medroxy-progesterone acetate, dimethisterone, ethynodoil diacetate, and chlormadinone acetate, norethindrone acetate and ethynylestradiol.

Other drugs which can be incorporated in the systems of this invention include: drugs for reducing blood pressure such as those described in U.S. Pat. No. 3,469,005; pharmaceutical compositions for the control of appetite such as the combinations of amphetamines and thioridazines described in U.S. Pat. No. 3,495,005; and, agents for treating psychosis in mammals such as those described in U.S. Pat. No. 3,495,007.

Also contemplated for use herein are prodrugs and their biologically active metabolites either of which may be an effective therapeutic active ingredient in accordance with this invention, such as, for example, naltrexone and one of its pharmaceutically active metabolites six-$\beta$-naltrexone The above listing of drugs is not intended to be comprehensive, but merely representative of the wide variety of drugs and biologically active substances which can be used with this invention. Those skilled in the art will know or be able to determine by routine experimentation that many other specific drugs are and/or biologically active substances also suitable.

As discussed hereinabove, the amount of drug dispersed in the inventive implant will depend, of course, on many factors including the specific drug, the function to be accomplished, the length of time it is desired to dispense the drug, the amount of drug to be dispensed in a specific time, the size of the device, and many other factors. In general, amounts ranging from about 0.01% to about 99.9% by weight of the device can be incorporated.

The amount of drug to be dispensed in a specified time, will of course, depend on such factors as the particular application, the particular drug, the age of the patient, etc. In general, what will constitute an "effective amount" will be known or easily ascertainable by those skilled in the art. Much of this type of data is published in the literature or easily determined by routine experimentation. Examples of the published literature on effective amounts of progestin-type steroids, in this case for topical application, can be found in Shipley, "Effectiveness of Topically Applied Progestational Agents," *Steroids* 7 (4): 341–349, (April 1966). In a like manner, the following literature describes effective amounts of addictive drug antagonists: MARTIN, W. R., "Opioid Antagonists," *Pharmacological Reviews,* Vol. 19, no. 4, pp. 463–521 (1967) and references contained therein; FREEDMAN, A. M., "Cyclazocine and Methadone in Narcotic Addiction," *The Journal of the American Medical Association,* Vol. 202, pp. 191–194 (Oct. 16, 1967). Also, the patents mentioned above often contain data on effective amounts for any particular application.

In addition to the control over delivery of drugs which can be obtained through proper choice and design of the inventive implant as discussed supra, the dosage administered by this implant can be controlled by the size and shape of the implant device, concentration of the drug in the device, density of the device, and nature of the carrier surface area, pore size, matching of the carrier and drug, nature of the surroundings, etc. This is of a particular advantage where it is desirable to deliver a metered amount of the drug over a specified period of time.

Of course, combinations of drugs and substances in addition to drugs can also be incorporated into the inventive implant device. For example, radioactive tracers such as carbon-14, nonradioactive tracers such as barium sulfate, carriers which would transport the drug through skin such as dimethylsulfoxide and dimethylsulfone, water-soluble excipients, etc. could be incorporated with certain drugs for particular applications. The amount of auxiliary agent used will depend, of course, on the specific agent, drug and carrier used to fabricate the implant device as well as the purpose for incorporating the auxiliary agent.

In accordance with a preferred aspect the present invention, there is provided an opiate antagonist implant in the form of a pellet in which the active ingredient antagonist is present in concentrated form as a self-sustaining delivery mechanism for its own dissolution and for delivering an effective amount of an opiate antagonist over a prolonged or extended period of time, preferably in excess of thirty days and more preferably in excess of ninety days. The implant is adapted to be implanted subcutaneously.

In a surprising and unexpected development of the present invention, it has been found that the use of an anti-inflammatory compound, particularly a steroid, in admixture combination with a pharmaceutical or biologically active substance, particularly an opiate antagonist, and a pharmaceutical carrier compressed into a pellet provides for unexpectedly long-lasting dosing times, such as, for example, up to approximately eighty days and longer, thus providing for particularly efficacious drug delivery periods, for example, slow-release antagonist delivery for anti-readdiction therapy as the case may be.

Any anti-inflammatory agent may be used in this invention, including without limitation, any compound that is effective to reduce blood flow to cellular elements, whether steroidal or non-steroidal, i.e., non-steroidal anti-inflammatory delivery (NSAID). By way of example only, some steroids useful herein include betamethasone dipronionate, betamethasone phosphate, betamethasone valerate, clobetasol propionate, cortisone acetate, dexamethasone phosphate acetate, dexamethasone micronized, fluocinonide, hydrocortisone acetate, hydrocortisone sulfate, methyl prednisone acetate, and triamcinolone acetonide.

The amount of anti-inflammatory compound may also vary widely depending upon such diverse factors as the specific active ingredient or drug employed, the density of the implant, the amount of drug to be released in a desired time, the size of the implant and many other factors, all of which are within the realm of consideration of the ordinary skilled practitioner to provide the desirable amount of anti-inflammatory agent for any given situation without undue experimentation. In general, amounts ranging from about 0.01% to about 99.9% by wt may be employed.

Any pharmaceutically acceptable carrier or filler may be used in accordance with this invention, including without limitation, magnesium stearate, stearic acid, starch, and cellulose. A preferred carrier is magnesium stearate which is often used as both a lubricant and a binder in tablets, and is particularly preferred because of its decreased solubility in physiological media providing for prolonged implant dissolution and extended drug delivery times, thus enabling the desired therapeutic drug level in a patient's bloodstream for a desired amount of time.

The respective amounts of active ingredient and binder/anti-inflammatory compound may vary from about 0.01% active ingredient/99.9% binder/anti-inflammatory compound by wt to about 99.9% active ingredient/0.01% binder/anti-inflammatory compound by wt, with the preferred active ingredient range being from about 45% wt to about 95% wt with the remainder carrier or filler material/binder and anti-inflammatory compound.

Further in accordance with the present invention is the unexpected and surprising effect of using compression of the admixture of active ingredient, anti-inflammatory agent and pharmaceutical carrier to form the subcutaneously implantable drug delivery devices, e.g., implants, of the invention which are able to dispense therapeutically effective amounts of active ingredient over heretofore unknown extended periods of time. Without intending to limit this invention to any particular theory, it is thought that compression used to form, for example, an implantable drug delivery device, provides for a smaller surface area, concomitantly decreasing solubility and thus providing less material per time that can be attacked or be subjected to phagocytosis once implanted. It is also thought that the large size of carrier particles in comparison to the relatively smaller size of drug particles will also provide for longer drug dispersion due to shielding from phagocytosis.

These surprising and unexpected results of the present invention are more fully discussed hereinbelow.

As shown, the presently inventive implants advantageously avoid the use of conventional complex copolymer delivery systems, polymer matrices, encapsulating agents and other expensive and complex time-release agents, which have been found to produce unacceptable complications in humans in earlier studies, along with relatively short dosage release times. The inventive implants are easily manufactured with active ingredient in concentrated form for direct subcutaneous implantation in humans to treat a great variety of maladies.

A convenient avenue to more fully illustrate the present invention is to exemplify a preferred aspect of the invention, which is an opiate antagonist implant comprising an admixture of an opiate antagonist, an anti-inflammatory agent and a pharmaceutically acceptable carrier, and which is prepared by compressing the admixture into a subcutaneously implantable pellet containing antagonist in concentrated form as exemplified hereinbelow. While implanted in a patient, the pellet dissolves, releasing over the desired length of time, such as up to and exceeding eighty days, therapeutic amounts of opiate antagonist effective to block the effects of opiates on the human nervous system, and is effective in inhibiting the effects of endogenous, exogenous, synthetic and natural opiates, and is also effective in inhibiting the effects of a number of other addictive substances including cocaine, alcohol and nicotine A variety of opiate antagonists can be utilized in the implants of this invention, any of which is not critical to the practice of this invention. Representative examples of such opiate antagonists include, but are not limited to, naltrexone, naloxone, cyclazocine, diprenorphine, metazocine, levallorphan, metazocine, nalorphine, nalmefene, and salts thereof, including any pharmaceutically active metabolites. A preferred opiate antagonist is naltrexone, which has received FDA approval for use in humans and has been shown to be free of severe side-effects. Naltrexone is neither addicting nor habit-forming.

A preferred embodiment for manufacturing the inventive opiate antagonist implant, illustrating naltrexone as the opiate antagonist, triamcinolone acetonide as the steroidal anti-inflammatory agent and magnesium stearate as the carrier, is described in Example 1 below.

It is to be understood however, that this Example is for illustrative purposes only and is not intended to limit the scope of this invention or the claims in any way.

EXAMPLE 1

Materials Preparation
Preparation of Naltrexone Free Base Ingredients
    106 ml 10% NaOH solution
    100 g Naltrexone HCl (Ntx-HCl)
    1000 ml distilled $H_2O$
    Gauze and filter paper/large glass funnel
    green marble table
Preparation of 10% Sodium Hydroxide
    110 ml Distilled $H_2O$
    11 g NaOH crystals 110 ml distilled H$_2$O is placed in a 300 ml beaker, and 11 g of crystals is slowly added over 3–4 minutes, and the solution stirred until needed.

Preparation of Filtering Apparatus

Two 4×4 gauze sponges are unfolded and used to line the inside of the large funnel, placing each one at right angles to one another. A folded sponge is then laid in the center of the funnel. A large piece of filter paper is folded into quarters, then opened into a cone shape. This is placed inside of the funnel on top of the gauze. Make sure the edges of the unfolded gauze can be grasped once the filter paper is filled. When filling, it is preferred to direct the inside tab of the filter paper toward the center of the cone for better drainage of the supinate.

Preparation of Ntx-HCl Slurry 100 g Ntx-HCl 300 ml distilledH$_2$O 100 ml distilled H$_2$O is added to a large beaker, then approximately one-half of the Ntx-HCl powder is added. A hard substance forms. The Ntx-HCl is broken up into smaller fragments, and another 100 ml of water is added. The remaining Ntx-HCl powder is then added to the slurry and the above repeated. Once the pieces are of less than about ¼" diameter, a hand blender can be used to further break up the slurry into fine pieces for 5 minutes. The blender is continued to be used on the milky slurry as the remaining 100 ml of water is slowly added over 4–5 additional minutes.

Precipitation of Naltrexone Base 106 ml 10% NaOH

Ntx-HCl slurry 4 ml of the freshly made NaOH is discarded. While continuing blending the slurry with the hand blender, approximately 30–40 ml of 10% NaOH is added to the slurry. The slurry will change consistency to paste-like. Blending is continued for another 2–3 minutes, then another 30 ml of NaOH added while blending, and blending then continued for an additional 2–3 minutes, and the blender removed. Continue adding the NaOH in 10 ml aliquots while constantly stirring with a spatula. After the last aliquot is added, stirring is continued until it is mixed, then the slurry is immediately dumped into the prepared filtering apparatus. Rinse out the flask with distilled H$_2$O and dump into the funnel. Once the supernate has drained off, wash the recovered Ntx base with 150 ml of distilled H$_2$O four times. The gauze liner may be used to gently squeeze the filter paper together to facilitate drainage. Once the washings are complete, lift the filter paper out of the funnel, and dump the Ntx onto the marble a drying table, preferably marble. Spread the base uniformly over the table and let dry overnight. When dry, scrape the NTX base up and weigh. The resultant weight in grams divided by 100 equals the percent yield.

EXAMPLE 2

Preparation of Naltrexone Pellet Mixture

Triamcinolone acetate powder (TCN)

Magnesium Stearate Powder (MgS)

1 mm coarse filtering screen

Fine filtering screen

The entire recovered NTX base is sifted through the coarse screen to break up large chunks and to remove any cotton fiber or filter paper contaminants.

Each pellet will contain approximately 900 mg of NTX base and approximately 10 mg of TCN. Each pellet also comprises a mosaic of particles with a variable amount of MGS as a binder and hydrophobic agent in a total ratio of approximately 10:1.

Calculation of Pellet Yield

Divide the weight of the recovered base by 0.9 (units=grams)

$$\frac{\text{yield}}{0.9} = \text{Total number of pellets } (P_t)$$

Calculation of TCN Addition $$TCN(g) = 0.010 \text{ g} \times P_t$$

Measure this weight of TCN, sift, and add to the total amount of NTX. Mix the powders thoroughly. Afterward, divide the mixture into 2 separate halves ($\alpha$ and $\beta$).

Calculation of Mg Stearate Addition

The total amount of MgS per lot of NTX will be in a 10:1 ratio:

$$\text{yield} = MgS_{t(g)}$$

The total amount of MgS added to the $\alpha$ NTX fraction will be in a 15:1 ratio by weight:

$$NTX\alpha = MgS\alpha(g)$$

The total amount of MgS added to the $\beta$ NTX fraction will be in a 10:1 ratio by weight:

$$\frac{NTX\beta}{10} = MgS\beta(g)$$

The calculated amount of MgS is to be added to each NTX fraction, and mixed throughly, then pressed into large pellets separately. They are then crushed and sifted with the course screen to make fragments no larger than 1 mm diameter. The fractions are then combined along with the remainder of the MGS:

$$\text{Remaining } MgS(g) = MgS_t - (MgS(\alpha) - MgS_\beta)$$

This is the mixture that will be used for pellet manufacture.

EXAMPLE 3

Pellet Manufacture

In accordance with this invention, pellets may be made using any conventional device, such as, preferably, a Parr pellet press® (Parr Instrument Company). Following the standard procedure for mixing the NTX Base preparation, 1.003 g of mixture is required for a pellet containing 900 mg. Using a tarred scale, 1.005–1.010 g is measured (to allow for chipping of the pellet during the manufacturing process and drift of the scale) and is then placed into a custom die mold (FIG. 1). In FIG. 1, relative dimensions (millimeters) of a die mold customized for use in accordance with the invention are shown. The dimensions preferably vary by about 10% without having much impact on the quality of the pellet produced. Preferably, the pellets produced from this mold should be 1.5–1.7 mm in length if the proper amount of compression is used on the press. Also, in this embodiment the shape of the pellet formed is slightly conical, being slightly larger in diameter at the end that was compressed against the collar. There may also be a small lip produced around this surface formed by powder being forced out of the space formed between the mold and collar. This lip often gets chipped off during its penetration into the insertion device, hence the extra weight added to the mold.

The conical nature of the pellet becomes important during its placement within the insertion device. Care must be taken to insert the narrow end of the pellet first into the device. As shown in FIG. 1, there is cylindrical shaped body 2, shown in cross-sectional cutaway 4 with dimensions (mm) and a conically-shaped top portion 6 (die mold) for receiving powder to be compressed into a pellet.

There are many factors that affect the quality of the pellets. The most important of these is the inner surface of the die mold. It is preferably smooth and polished, otherwise an inordinate number of pellets will break during extraction. During the manufacture, if this becomes an acute problem, it is an indication the die needs to be resurfaced and polished. Die molds made of hardened 17–4PH stainless steel require resurfacing less often, and appear to produce a superior pellet. The compressing piston should also be made of hardened surgical steel and fit tightly against the walls of the die to prevent caking of the NTX around it and against the cylinder walls. Small granules also make a harder pellet less prone to break than the powder form of the preparation, or from large chunks obtained after the first compression. Thus using a screen allowing only particles that are 1 mm or less is employed. The entire volume of the weight of the pellet should fit into the compression cylinder of the die with minimal hand tamping, and without the need to partially compress the contents using the machine. Finally, extraction of the pellet should be accomplished in the same direction as compression. Failure to follow these guidelines may result in a pellet that is at greater risk for breaking into fragments during extraction, placement into the insertion device, packaging and shipping, during insertion into the patient, or during the patients usual daily activity once home. There is evidence to suggest tissue absorption of the pellet will occur more quickly if the pellet fragments once inserted, thus decreasing the therapeutic longevity of the NTX-T® pellet.

Packaging and Sterilization

The drug delivery devices produced in accordance with this inventiion, for example, the pellets dscribed herein, should be sterilized before insertion into a body portion. This is preferably accomplished according to the following procedure. Each NTX-T® Pellet is placed into a self-sealing pouch (Moore Medical) and labeled with the proper identification and lot number. Once a sufficient amount of packets have been prepared, they are shipped to Isomedix Corporation for gamma irradiation sterilization (7 kilorads for 6 hours). When the shipment returns to the office, they are stamped indicating they have been sterilized with gamma irradiation. The product is now ready for clinical use.

EXAMPLE 4

Manufacture of the Insertion Device

An insertion device useful and preferred for inserting the inventive drug delivery devices, for example, the illustrated pellets, is described below.

Materials 3 cc syringes (Becton Dickinson PrecisionGlide®)

Heavy duty blade cutters

Alcohol flame

Procedure

Pull back the plunger on the syringe to the 1.5 cc mark, then carefully heat the area of the syringe between the 1 cc mark and the hub. The barrel should be hot to the touch, but not beginning to melt. A faint discoloration of the plastic may appear.

Position the syringe such that the finger rest opposite the 1 cc mark is pointed toward you while grasping the syringe by the needle covering.

Use the heavy cutters to cut the tip of the syringe off on an angle using the 1 cc line and the tip of the hub as landmarks. Discard the end and needle into the sharp container.

If cut has been made properly, the physician using the device will be allowed to use the graduations from the syringe as a measure as to how far under the skin the device is.

Placement of the Pellets into the Insertion Device

Materials

Prepared insertion device

Alcohol flame

Dilator/impactor

Prepared pellets

Procedure

Heat the insertion device over the alcohol flame until hot and pliable, but not melting.

Dilate the tip of the device with the dilator by inserting it approximately 5 mm into the barrel. Let the device cool for 15 seconds before removing the dilator.

Carefully place the pellet narrow end first inside the barrel of the insertion device. Use the dilator to move it completely into the barrel, passed the proximal lip of the device.

EXAMPLE 5

Clinical Use

In use, the pelletized opiate antagonist can be subcutaneously implanted in an addict as part of a detoxification program or once a patient has completed a detoxification program. Once implanted, opiate antagonist will be released into the patient's bloodstream for an extended period of time. Such time will depend on the size of the pellet inserted in addition to the type and the percentage of the opiate antagonist contained therein. For example, a pellet comprising approximately 95% naltrexone, which is approximately 8 mm long and has a diameter of approximately 13 mm, will supply therapeutic amounts of the opiate antagonist for up to one month or longer. The delivery of sufficient levels of the opiate antagonist in the patient eliminates the mood-altering effects of any opiate that the patient takes, and will help to maintain sobriety while the patient seeks counseling. It has also been discovered that the implant is also useful in eliminating the mood-altering effects of cocaine, alcohol, and nicotine. To increase the period of time in which naltrexone will be effectively delivered into a patient's bloodstream and to effectively block the positive reinforcement from the particular drug, larger pellets may be manufactured and implanted.

To exemplify the antagonist effects of naltrexone, the following Table I summarizes the effect of therapeutically effective blocking normally lethal does of 5 cc of Fetanyl IV on eight patients subcutaneously implanted with a compressed a pelletized opiate naltrexone composition which lacks an anti-inflammatory agent.

TABLE I

Fentanyl Challenges Post-Implant

| Patient | Age | Sex | Challenge Date | # of Days Post-Implant | Pupillary Size (mm) pre | Pupillary Size (mm) post | Rsp. Rate pre | Rsp. Rate post | Response |
|---|---|---|---|---|---|---|---|---|---|
| 1 | 30 | m | 12-16-96 | 30 | 2–3 | 2–3 | 18 | 18 | none |
| 2 | 36 | f | 12-18-96 | 31 | 3–4 | 3–4 | 16 | 18 | slight dizziness, light-headed 1 minute post-injection |
| 3 | 33 | f | 12-30-96 | 38 | 2–3 | 2–3 | 16 | 16 | no change, no effect, + pus |
| 4 | 28 | f | 01-02-97 | 28 | 2–3 | 2–3 | 20 | 20 | c/o light-headed, otherwise negative |
| 5 | 28 | m | 01-02-97 | 28 | 2–3 | 2–3 | 20 | 20 | + nausea, possible vagal response, otherwise negative |
| 6 | 36 | m | 01-03-97 | 37 | 2–3 | 2–3 | 20 | 20 | |
| 7 | 39 | m | 01-10-97 | 30 | 2–3 | 2–3 | 16 | 20 | none |
| 8 | 17 | m | 01-13-97 | 30 | 3–5 | 3–4 | 16 | 16 | slight dizziness, slight pupillary change |
| 9 | 30 | m | 01-20-97 | 38 | 2–3 | 2–3 | 20 | 20 | none |
| 10 | | f | 01-23-97 | 38 | 2–3 | 2–3 | 20 | 20 | none |
| 11 | | | 01-28-97 | 62 | 2–3 | 2–3 | 20 | 20 | none |
| 12 | | | 02-05-97 | 41 | 3 | 3 | 18 | 18 | none |
| 13 | | | 02-10-97 | 75 | 2–3 | 2–3 | 20 | 20 | none |
| 14 | | m | 02-11-97 | 22 | 2–3 | 2–3 | 16 | 16 | none |

In accordance with the present invention, the presently inventive antagonist implants unexpectedly provide for high therapeutic levels of antagonist in a patient's bloodstream over heretofore unobtainable periods of time. For example, a 1000 mg dose of naltrexone has been shown to provide for therapeutically effective levels of naltrexone leveling off rapidly if not immediately to ~2–8 ng/ml for approximately eighty days in a patient's bloodstream. In contrast, 1000 mg of naltrexone administered orally typically provides 100 ng/ml in a patient's bloodstream for 48 hours, then leveling off to 0 mg/ml such that after two days there is no dose of antagonist and thus no anti-addiction therapy. Furthermore, it has been found that such conventional oral methods of naltrexone delivery supplying approximately 100 ng/l in the blood stream oftentimes results in undesirable side effects such as an unpleasant feeling, rendering patients reluctant to take the drug. Such can hardly be said to provide for effective anti-readdiction therapy.

The following Table II summarizes patients' blood level results after administration of a pellet produced in accordance with the present invention, as in Examples 1–4. The data in Table II demonstrates the unexpected and surprising results achieved from the present inventive implant in maintaining therapeutic blood levels of opiate antagonist in excess of seventy-five days. Again, without intending to limit this invention to any particular theory, it is thought that the unexpectedly long inventive implant therapeutic delivery durations are due to several factors, one being the relative insolubility in physiological media of the active ingredient, e.g., opiate antagonist, and the relative insolubility of the anti-inflammatory agent and the pharmaceutically acceptable carrier, or binder/lubricant, e.g., magnesium stearate, all of which provide for delayed release of therapeutic amounts of active ingredient. As also discussed above, compression of the implant admixture is thought to contribute to delayed release time and long-acting activity of the inventive implants.

In addition to the above, the therapeutic longevity of the inventive implants is also thought to be attributed to, at least in part, the specific manufacturing process of the implants and their resulting crystalline distribution makeup. As described hereinabove, in one preferred embodiment of the invention, as conveniently illustrated by the production of an opiate antagonist-comprising implant, naltrexone antagonist plus carrier/binder/lubricant, e.g., magnesium stearate, plus anti-inflammatory agent, e.g., steroid, are admixed and compressed into pellets. These pellets are then crushed and admixed with additional magnesium stearate and them compressed again into an implantable pellet. This process results in a pellet having distinctly different population sizes of granules with different sized granules in different concentrations/ratios of active ingredient, anti-inflammatory agent and binder/lubricant. Once more, without intending to limit this invention to theory, it is thought that there exists a population of mixed granule sizes in different ratios/concentrations of active ingredient, anti-inflammatory agent and binder/lubricant/carrier, and a second population resulting from crushing the first pelletized admixture, admixing with additional binder/lubricant and compressing into an implantable pellet, the second population thereby being at least a portion of the first population coated with additional binder. Such different size populations of granules with different concentrations/ratios of materials is thought to act in delaying the absorption of the implanted pellet and provide for the unexpected and surprisingly extended therapeutic efficacy of the inventive implants.

In an additional aspect of the instant invention, the subcutaneously implantable opiate antagonist-comprising pellet is contemplated for use as a stand-alone treatment for opiate dependent patients, and/or a first-line treatment for use in conjunction with various detoxification procedures, such as described in U.S. Pat. No. 5,789,411, DETOXIFICATION UNDER GENERAL ANESTHESIA THERAPY, the entire disclosure of which is incorporated by reference herein. For example, the presently inventive pellets may be used for detoxification, sending a patient into withdrawal. If desired, the patient's withdrawal symptoms may be ameliorated with medication, or, for example, by detoxification under the aforesaid method, or by first detoxifying the patient under general anesthesia, and following up by subcutaneously implanting the inventive opiate antagonist comprising pellets as an anti-readdiction maintenance therapy to ensure compliance with opiate addiction rehabilitation.

The results of Table II are set forth below:

TABLE II

| | |
|---|---|
| 1. | Date of implant: 5-7-98 |
| | Date: 6-13-98 |
| | Days since implant: 37 |
| | Ntx level $\leq 3$ ng/ml |
| | 6-beta-ntx level $\underline{3}$ ng/ml |
| 2. | Date of implant: 5-7-98 |
| | Date: 6-19-98 |
| | Days since implant: 33 |
| | Ntx level $\leq 2$ ng/ml |
| | 6-beta-ntx level $\underline{3}$ ng/ml |
| 3. | Date of implant: 5-7-98 |
| | Date: 6-16-98 |
| | Days since implant: 30 |
| | Ntx level $\underline{3}$ ng/ml |
| | 6-beta-ntx level $\underline{4}$ ng/ml |
| 4. | Date of implant: 5-7-98 |
| | Date: 6-15-98 |
| | Days since implant: 29 |
| | Ntx level $\underline{2}$ ng/ml |
| | 6-beta-ntx level $\underline{5}$ ng/ml |
| 5. | Date of implant: 5-7-98 |
| | Date: 5-29-98 |
| | Days since implant: 22 |
| | Ntx level $\underline{7}$ ng/ml |
| | 6-beta-ntx level $\underline{9}$ ng/ml |
| 6. | Date of implant: 5-7-98 |
| | Date: 5-21-98 |
| | Days since implant: 14 |
| | Ntx level $\underline{11}$ ng/ml |
| | 6-beta-ntx level $\underline{11}$ ng/ml |
| 7. | Date of implant: 5-2-98 |
| | Age: 43 |
| | Date: 7-18-98 11 am before new pellet |
| | Days since implant: 77 |
| 8. | Date of implant: 5-2-98 |
| | Age: 43 |

TABLE II-continued

| | |
|---|---|
| | Date: 7-11-98 |
| | Days since implant: 70 |
| | Ntx level $\underline{3}$ ng/ml |
| | 6-beta-ntx level $\underline{7}$ ng/ml |
| 9. | Date of implant: 5-2-98 |
| | Date: 7-18-98 |
| | Days since implant: 67 |
| | Ntx level $\leq 4$ ng/ml |
| | 6-beta-ntx level $\underline{8}$ ng/ml |
| 10. | Date of implant: 5-2-98 |
| | Date: 6-20-98 |
| | Days since implant: 49 |
| | Ntx level $\underline{4}$ ng/ml |
| | 6-beta-ntx level $\underline{14}$ ng/ml |
| 11. | Date of implant: 5-2-98 |
| | Date: 6-13-98 |
| | Days since implant: 42 |
| | Ntx level $\underline{4}$ ng/ml |
| | 6-beta-ntx level $\underline{11}$ ng/ml |
| 12. | Date of implant: 5-2-98 |
| | Date: 6-6-98 |
| | Days since implant: 35 |
| | Ntx level $\underline{4}$ ng/ml |
| | 6-beta-ntx level $\underline{13}$ ng/ml |
| 13. | Date af implant: 5-7-98 |
| | Age: 19 |
| | Weight: 90 lbs. × 2.2 = 41 kg |
| | Date: 7-11-98 |
| | Days since implant: 65 |
| | Ntx level $\leq 2$ ng/ml |
| | 6-beta-ntx level $\underline{2}$ ng/ml |
| 14. | Date of implant: 5-7-98 |
| | Age: 19 |
| | Weight: 90 lbs. × 2.2 = 41 kg |
| | Date: 7-18-98 |
| | Days since implant: 62 |
| | Ntx level $\leq 4$ ng/ml |
| | 6-beta-ntx level $\leq 4$ ng/ml |
| 15. | Date of implant: 5-7-98 |
| | Age: 19 |
| | Weight 90 lbs. × 2.2 = 41 kg |
| | Date: 6-27-98 |
| | Days since implant: 51 |
| | Ntx level $\underline{8}$ ng/ml |
| | 6-beta-ntx level $\underline{8}$ ng/ml |
| 16. | Date of implant: 5-7-98 |
| | Date: 6-20-98 |
| | Days since implant: 44 |
| | Ntx level $\underline{3}$ ng/ml |
| | 6-beta-ntx level $\underline{5}$ ng/ml |
| 17. | Date of implant: 5-7-98 |
| | Date: 6-13-98 |
| | Days since implant: 37 |
| | Ntx level $\underline{3}$ ng/ml |
| | 6-beta-ntx level $\underline{3}$ ng/ml |
| 18. | Date of implant: 5-7-98 |
| | Date: 6-6-98 |
| | Days since implant: 30 |
| | Ntx level $\underline{4}$ ng/ml |
| | 6-beta-ntx level $\underline{8}$ ng/ml |
| 19. | Date of implant: 5-7-98 |
| | Date: 5-29-98 |
| | Days since implant: 22 |
| | Ntx level $\underline{8}$ ng/ml |
| | 6-beta-ntx level $\underline{11}$ ng/ml |
| 20. | Date of implant: 5-7-98 |
| | Date: 5-15-98 |
| | Days since implant: 8 |
| | Ntx level $\underline{7}$ ng/ml |
| | 6-beta-ntx level $\underline{17}$ ng/ml |
| 21. | Date of implant: 6-15-98 |
| | Age: 46 |
| | Weight 200 lbs × 2.2 = 4.400 kg |
| | Date: 7-13-98 |
| | Days since implant: 28 |
| | Ntx level $\underline{2}$ ng/ml |
| | 6-beta-ntx level $\underline{7}$ ng/ml |
| 22. | Date of implant: 5-28-98 |
| | Date: 6-11-98 |

TABLE II-continued

|  |  |
|---|---|
|  | Days since implant: 14<br>Ntx level 8 ng/ml<br>6-beta-ntx level 15 ng/ml |
| 23. | Date of implant: 5-16-98<br>Date: 6-15-98<br>Days since implant: 30<br>Ntx level 3 ng/ml<br>6-beta-ntx level 6 ng/ml |
| 24. | Date of implant: 5-26-98<br>Date: 6-25-98<br>Days since implant: 30<br>Ntx level 14 ng/ml<br>6-beta-ntx level 4 ng/ml |
| 25. | Date of implant: 5-19-98<br>Age: 22<br>Date: 6-22-98<br>Days since implant: 34<br>Ntx level 4 ng/ml<br>6-beta-ntx level 7 ng/ml |
| 26. | Date of implant: 6-1-98<br>Age: 28 (today)<br>Weight 180+ lbs. × 2.2 = 82 kg<br>Date: 7-8-98<br>Days since implant: 38<br>Ntx level ≤2 ng/ml<br>6-beta-ntx level 5 ng/ml |
| 27. | Date of implant: 6-9-98<br>Age: 18<br>Date: 7-11-98<br>Days since implant: 32<br>Ntx level 7 ng/ml<br>6-beta-ntx level 21 ng/ml |
| 28. | Date ot implant: 6-10-98<br>Age: 52<br>Weight 235 lbs. × 2.2 = 107 kg<br>Date: 7-9-98<br>Days since implant: 29<br>Ntx level 4 ng/ml<br>6-beta-ntx level 9 ng/ml |
| 29. | Date of implant: 5-28-98<br>Age: 20<br>Weight 117 lbs. × 2.2 = 53 kg<br>Date: 7-6-98<br>Days since implant: 39<br>Ntx level 5 ng/ml<br>6-beta-ntx level 9 ng/ml |
| 30. | Days since implant: 78<br>Ntx level 4 ng/ml<br>6-beta-ntx level 4 ng/ml |
| 31. | Days since implant: 55<br>Ntx level 36 ng/ml<br>6-beta-ntx level 14 ng/ml |
| 32. | Days since implant: 44<br>Ntx level 11 ng/ml<br>6-beta-ntx level 10 ng/ml |
| 33. | Days since implant: 60<br>Ntx level 10 ng/ml<br>6-beta-ntx level 8 ng/ml |
| 34. | Days since implant: 78<br>Ntx level 6 ng/ml<br>6-beta-ntx level 11 ng/ml |
| 35. | Days since implant: 67<br>Ntx level 26 ng/ml<br>6-beta-ntx level 14 ng/ml |
| 36. | Days since implant: 77<br>Ntx level 2 ng/ml<br>6-beta-ntx level 6 ng/ml |

EXAMPLE 6

Relapse Studies

Relapse is common after detoxification. Naltrexone maintenance therapy has been used to decrease the incidence of relapse but requires (1) a period of abstinence after detoxification and (2) compliance with the medical regimen. Detoxification under general anesthesia eliminates the need for a period of abstinence. This study evaluates the effectiveness of the inventive depot naltrexone preparation to eliminate non-compliance with the medical regimen after detoxification under general anesthesia.

Two randomly selected sequential groups of opiate addicts were chose from a population of 952 patients (mean age 36, 75% male) who underwent opiate reversal under general anesthesia (ORGA) with immediate initiation of naltrexone maintenance therapy. The first group (ONM) received naltrexone maintenance therapy by oral administration of 50 mgs of naltrexone per day. The second group (DNM)received naltrexone maintenance through a depot naltrexone preparation containing 1000 mgs of naltrexone per month, via a pellet implant used in Table I.

There were 434 patients in the ONM group and 199 patients in the DNM populations with respect to age, sex, type of opiate use or amount of use.

Telephone follow-up was attempted for 633 patients. Because a large number of the total populations were not available for follow-up, comparative analysis of those using opiates for the two populations (DNM versus ONM) were made in three ways with the following results; namely (1) excluding those who could not be contacted—19% versus 44% with $x2=14.06$ (very significant); (2) assuming all those not contacted were using at one month after opiate reversal—50% versus 54% with $x2=0.76$ (not significant), and (3) assuming all those not contacted were clean one month after opiate reversal—9% versus 14% with $x2=18.5$ (very significant).

The results of this study show that the subcutaneously implantable naltrexone-containing pellets of this invention decreased relapse significantly immediately post-detoxification from opiates.

Turning to another aspect of this invention, deep tissue infections such as that of bone (osteomyelitis) require extensive exposure to antibiotics. This is classically done by giving intravenous antibiotics over an extended period of time in order to maintain exposure of the infected area to antibiotics which are more in the blood. This method is cumbersome and results in expensive antibiotics exposure to the rest of the body. Therefore, in accordance with this invention, it is advantageous to implant a pellet comprising an antibiotic in an area adjacent to such an infection so that the highest concentration of antibiotic would be at the actual site of the infections, near the pellet. This could be maintained for a prolonged period of time with minimal exposure of the rest of the body to the higher concentrations of antibiotic, and avoid the cumbersome necessity of intravenous administration. Such pellets can be prepared in a manner using the method described above employing a binder and anti-inflammatory agent. Such pellets can be prepared in similar manner as described above employing a binder and anti-inflammatory agent and compressed into a slow-release drug delivery vehicle.

Further in accordance with yet another aspect of this invention, in administering chemotherapeutic agents to patients, such agents kill not only the tumor but fast growing cells which are exposed to the high concentrations of the agent throughout the body. Thus, in accordance with this invention, it is advantageous to implant a pellet comprising the chemotherapeutic agent in a region of or adjacent to the tumor, such that the rest of the body would only be exposed to a higher concentration, thereby having an increased killing power at the site and prolonged action, leaving the rest of the body exposed to lesser dosages. This would also eliminate the need for cumbersome repeated administrations of these drugs which are often administered intravenously in patients whose vascular system is somewhat compromised from repeated injections of these agents.

The present invention may be embodied in many other specific forms employing any of the pharmaceutical/bioactive agents mentioned hereinabove in combination with an anti-inflammatory agent and pharmaceutically acceptable carrier to provide a reliable time release of therapeutic amounts of active ingredient without departing from the spirit or essential attributes thereof.

What is claimed is:

1. An opiate antagonist subcutaneous implant comprising an admixture of an opiate antagonist, an steroidal anti-inflammatory agent and a pharmaceutically acceptable carrier.

2. The opiate antagonist implant of claim 1 wherein said implant is effective to release levels of said opiate antagonist over an extended period of time when subcutaneously implanted in a human in need thereof.

3. The opiate antagonist implant of claim 2 where said extended period of time is at least approximately 80 days.

4. The opiate antagonist implant of claim 1 wherein said opiate antagonist is selected from the group consisting of an endogenous, exogenous, synthetic and natural opiate antagonist.

5. The opiate antagonist implant of claim 1 wherein said opiate antagonist is selected from the group consisting of naltrexone, naloxone, nalmefene, cyclazocine, diprenorphine, metazocine, levallorphan, nalorphine, and salts thereof.

6. The opiate antagonist implant of claim 1 wherein said pharmaceutically acceptable carrier is magnesium stearate.

7. The opiate antagonist implant of claim 1 wherein said steroidal anti-inflammatory agent is triamcinolone acetate.

8. The opiate antagonist implant of claim 1 wherein said subcutaneously implant is cylindrical in shape, is approximately 8 mm long and has a diameter of approximately 13 mm.

9. The opiate antagonist implant of claim 1 wherein said opiate antagonist comprises from about 0.01% to about 99.9% of the implant by weight.

10. The opiate antagonist implant of claim 1 wherein said opiate antagonist comprises from about 45% to about 95% of the implant by weight.

11. The opiate antagonist implant of claim 1 wherein said subcutaneously implant has a hardness of in the range of about 12 to about 15 kiloponds.

12. A process of manufacturing an opiate antagonist subcutaneous implant comprising compressing a therapeutically effective amount of an opiate antagonist with an steroidal anti-inflammatory agent and a pharmaceutically acceptable carrier.

13. The process of claim 12 wherein the amount of said compression produces an implant which is effective to release said opiate antagonist in therapeutically effective amounts for at least about 80 days.

14. A process of manufacturing a naltrexone subcutaneous implant comprising the steps of:
(a) providing a quantity of naltrexone;
(b) providing a quantity of steroidal anti-inflammatory agent;
(c) providing a pharmaceutically acceptable carrier;
(d) admixing said anti-inflammatory agent with a pharmaceutically acceptable carrier and said naltrexone to form an admixture; and
(e) applying uniform pressure to the admixture of step (d) in order to obtain a naltrexone implant in the form of a pellet.

15. The method of claim 14 wherein approximately 1000 psi of pressure is applied to the admixture of step (d).

16. A method for administering an opiate antagonist to a human which comprises subcutaneously implanting the implant of claim 1 in a human.

17. The method of claim 16 wherein said implant comprises said opiate antagonist in an amount of from about 0.01 to 99.9% by weight.

18. The method of claim 16 wherein said opiate antagonist is selected from the group consisting of naltrexone, naloxone, nalmefene, cyclazocine, diprenorphine, etazocine, levallorphan, metazocine, nalorphine, and salts thereof.

19. The method of claim 16 wherein said pharmaceutically acceptable carrier is magnesium stearate.

20. The method of claim 16 wherein said wherein said implant releases therapeutically effective amounts of said antagonist to said human for at least approximately 80 days.

21. A method of treating an opiate addicted patient for opiate addiction comprising administering subcutaneously to the patient an opiate antagonist implant comprising an admixture of an opiate antagonist, an steroidal anti-inflammatory agent, and a pharmaceutically acceptable carrier.

22. A method of using an opiate antagonist implant comprising an admixture of an opiate antagonist, an steroidal anti-inflammatory agent, and a pharmaceutically acceptable carrier, wherein said method comprises subcutaneously implanting said implant in a patient in need thereof.

23. A method for detoxifying opioid-addicted a human comprising,
detoxifying said opioid-addicted human followed by administering the opioid antagonist implant of claim 1.

24. A method of maintaining an abstinent state in a human from opiate substance addiction or dependence comprising subcutaneously administering the opioid antagonist implant of claim 1 to said human.

25. A subcutaneous implant consisting essentially of an opiate antagonist, a steroidal anti-inflammatory agent and a carrier, wherein said opiate antagonist is a self-sustaining delivery mechanism for its own dissolution and delivery over time.

26. The implant of claim 25 wherein said implant is in the form of a pellet.

27. A method of increasing the duration of sustained release of therapeutically effective amounts of an opiate antagonist from an implant, comprising preparing an implant comprising an opiate antagonist, a steroidal anti-inflammatory agent and a carrier, and subcutaneously implanting the implant in a human in need thereof.

28. The implant of claim 1, which is in the form of a pellet.

29. The implant of claim 1, wherein said opiate antagonist comprises naltrexone.

30. The implant of claim 29, wherein said steroidal anti-inflammatory agent comprises triamcinolone acetate and said carrier is magnesium stearate.

31. The implant of claim 29, wherein said opiate antagonist comprises naltrexone, said steroidal anti-inflammatory agent comprises triamcinolone acetate, said carrier comprises magnesium stearate, and said implant is in the form of a pellet.

32. The process of claim 11, wherein said opiate antagonist comprises naltrexone, said steroidal anti-inflammatory agent comprises triamcinolone acetate, said carrier comprises magnesium stearate, and said implant is in the form of a pellet.

33. The process of claim 13, wherein said steroidal anti-inflammatory agent comprises triamcinolone acetate and said carrier comprises magnesium stearate.

34. A method for administering an opiate antagonist to a human which comprises subcutaneously implanting the implant of claim 31 in a human.

35. The method of claim 19, wherein said opiate antagonist comprises naltrexone, said steroidal anti-inflammatory agent comprises triamcinolone acetate, said carrier comprises magnesium stearate, and said implant is in the form of a pellet.

36. The method of claim 20, wherein said opiate antagonist comprises naltrexone, said steroidal anti-inflammatory agent comprises triamcinolone acetate, said carrier comprises magnesium stearate, and said implant is in the form of a pellet.

37. The method of claim 21, wherein said opiate antagonist comprises naltrexone, said steroidal anti-inflammatory agent comprises triamcinolone acetate, said carrier comprises magnesium stearate, and said implant is in the form of a pellet.

38. The method of claim 22, wherein said opiate antagonist comprises naltrexone, said steroidal anti-inflammatory agent comprises triamcinolone acetate, said carrier comprises magnesium stearate, and said implant is in the form of a pellet.

39. The implant of claim 25, wherein said opiate antagonist is naltrexone, said steroidal anti-inflammatory agent is triamcinolone acetate, said carrier is magnesium stearate, and said implant is in the form of a pellet.

40. The method of claim 27, wherein said opiate antagonist is naltrexone, said steroidal anti-inflammatory agent is triamcinolone acetate, said carrier is magnesium stearate, and said implant is in the form of a pellet.

* * * * *

UNITED STATES PATENT AND TRADEMARK OFFICE
CERTIFICATE OF CORRECTION

PATENT NO. : 6,203,813 B1
DATED : March 20, 2001
INVENTOR(S) : Gooberman

It is certified that error appears in the above-identified patent and that said Letters Patent is hereby corrected as shown below:

Title page,
Under "Related U.S. Application Data" and after "[63]", delete the 6 lines thereafter up to and including Jan. 13, 1997.

Column 1,
Delete lines 5-10.
Line 14, after "relates to", insert -- a --.
Line 34, "patients" should read -- patient's --.
Line 34, after "over", insert -- a --.

Column 3,
Line 7, after "references", insert a -- , --.

Column 4,
Line 62, "Adverse" should read -- Adversive --.

Column 5,
Line 2, after "said to", insert -- be --.

Column 6,
Line 2, after "ingredients", cancel -- and --.
Line 28, "ingredient" should read -- ingredients --.
Line 46, insert -- In -- before "U.S.".

Column 9,
Line 4, "a" should read -- an --.

Column 11,
Line 35, "an" should read -- and --.

Column 12,
Line 8, insert -- from -- after "different".

Column 13,
Line 39, "rugs" should read -- drugs --.

UNITED STATES PATENT AND TRADEMARK OFFICE
CERTIFICATE OF CORRECTION

PATENT NO. : 6,203,813 B1
DATED : March 20, 2001
INVENTOR(S) : Gooberman

It is certified that error appears in the above-identified patent and that said Letters Patent is hereby corrected as shown below:

Column 14,
Line 11, cancel "are".
Line 12, insert -- are -- after "substances".
Line 22, insert -- , -- after "will".

Column 16,
Line 34, insert -- . -- after "nicotine".

Column 17,
Line 50, cancel "the marble".

Column 19,
Line 33, "patients" should read -- patient's --.

Column 20,
Line 29, "passed" should read -- past --.
Line 63, "does" should read -- doses --.
Line 65, cancel "a".

Column 23,
Line 13, "is" should read -- are --.

Column 26,
Line 19, "were" should read -- was --.
Line 21, "were" should read -- was --.

Column 27,
Line 13, "an steroidal" should read -- a steroidal --.
Line 19, "where" should read -- wherein --.
Line 49, "with an" should read -- with a --.

UNITED STATES PATENT AND TRADEMARK OFFICE
CERTIFICATE OF CORRECTION

PATENT NO. : 6,203,813 B1
DATED : March 20, 2001
INVENTOR(S) : Gooberman

It is certified that error appears in the above-identified patent and that said Letters Patent is hereby corrected as shown below:

Column 28,
Line 14, cancel second occurrence of "wherein said".
Line 20, "an steroidal" should read -- a steroidal --.
Line 24, "an steroidal" should read -- a steroidal --.
Line 28, "detoxifying opioid-addicted a human" should read -- detoxifying an opioid addicted human --.

Signed and Sealed this

Sixth Day of November, 2001

*Attest:*

*Attesting Officer*

NICHOLAS P. GODICI
*Acting Director of the United States Patent and Trademark Office*